US008785152B2

(12) United States Patent
Yokoyama et al.

(10) Patent No.: US 8,785,152 B2
(45) Date of Patent: Jul. 22, 2014

(54) PROCESS FOR PRODUCTION OF NON-NATURAL PROTEIN HAVING ESTER BOND THEREIN (75) Inventors: Shigeyuki Yokoyama, Kanagawa (JP);
Kensaku Sakamoto, Kanagawa (JP);
Tatsuo Yanagisawa, Kanagawa (JP);
Takahito Mukai, Kanagawa (JP);
Takatsugu Kobayashi, Kanagawa (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 12/744,322

(22) PCT Filed: Nov. 21, 2008

(86) PCT No.: PCT/JP2008/071221
§ 371 (c)(1),
(2), (4) Date: Jul. 13, 2010

(87) PCT Pub. No.: WO2009/066761
PCT Pub. Date: May 28, 2009

(65) Prior Publication Data
US 2011/0136168 A1 Jun. 9, 2011

(30) Foreign Application Priority Data
Nov. 22, 2007 (JP) ................. 2007-302452

(51) Int. Cl.
C12P 21/00 (2006.01)
C12N 9/00 (2006.01)
C12N 15/52 (2006.01)
C12N 1/21 (2006.01)

(52) U.S. Cl.
USPC ....... 435/69.1; 435/325; 435/252.3; 435/183; 435/320.1; 536/23.2

(58) Field of Classification Search
None
See application file for complete search history.

(56) References Cited

U.S. PATENT DOCUMENTS

2006/0166319 A1  7/2006  Chan et al.
2009/0155844 A1  6/2009  Yokoyama et al.

FOREIGN PATENT DOCUMENTS

| EP | 1911840 A1 | 4/2008 |
| EP | 2192185 A1 | 6/2010 |
| JP | 2007037445 A | 2/2007 |
| WO | WO-2007/015527 A1 | 2/2007 |
| WO | WO-2007/099864 A1 | 9/2007 |

OTHER PUBLICATIONS (Triflates synthons for the synthesis of lysine analogues. Tetrahedron Letteres 40 (1999) 7083-7086).*

Synthesis of All Nineteen Appropriately Protected Chiral r-Hydroxy Acid Equivalents of the r-Amino Acids for Boc Solid-Phase Depsi-Peptide Synthesis Songpon Deechongkit, Shu-Li You, and Jeffery W. Kelly.*
Mapping Disulfide Connectivity Using Backbone Ester Hydrolysis. Pamela M. England Biochemistry 1999, 38, 14409-14415.*
An Expanded Set of Amino Acid Analogs for the Ribosomal Translation of Unnatural Peptides Oct. 2007 | Issue 10 pp. 1-15. Matthew C. T. Hartman.*
Hartman, M.C.T., et al., "An Expanded Set of Amino Acid Analogs for the Ribosomal Translation of Unnatural Peptides," PLoS One, vol. 2, No. 10, e972, pp. 1-15 (2007).
Wang, L., et al., "Expanding the genetic code," ChemComm, pp. 1-11 (2002).
Chapman, E., et al., "Mutational Analysis of Backbone Hydrogen Bonds in *Staphylococcal* Nuclease," J. Am. Chem. Soc., vol. 119, pp. 7151-7152 (1997).
Murakami, H., et al., "A highly flexible tRNA acylation method for non-natural polypeptide synthesis," Nature Methods, vol. 3, No. 5, pp. 357-359 (2006).
Kavran, J.M., et al., "Structure of pyrrolysyl-tRNA synthetase, an archaeal enzyme for genetic code innovation," PNAS, vol. 104, No. 27, pp. 11268-11273 (2007).
Koh, J.T., et al., "An Experimental Approach to Evaluating the Role of Backbone Interactions in Proteins Using Unnatural Amino Acid Mutagenesis," Biochemistry, vol. 36, pp. 11314-11322 (1997).
England, P.M., "Backbone Mutations in Transmembrane Domains of a Ligand-Gated Ion Channel: Implications for the Mechanism of Gating," Cell, vol. 97, pp. 89-98 (1999).
Wang, L., et al., "Expanding the Genetic Code of *Escherichia coli*," Science, vol. 292, pp. 498-500 (2001).
Office Action dated Sep. 20, 2011 filed in corresponding European Application No. 08 851 711.5.
Yanagisawa, T., et al., "Multistep Engineering of Pyrrolysyl-tRNA Synthetase to Genetically Encode $N^{\epsilon}$-(o-Azidobenzyloxycarbonyl) lysine for Site-Specific Protein Modification," Chemistry & Biology, vol. 15, pp. 1187-1197 (2008).
Liu & Shultz, "Adding New Chemistries to the Genetic Code," Annu. Rev. Biochem., pp. 15.1-15.32 (2010).
Tanrikulu, I. C., et al., "Discovery of *Escherichia coli* methionyl-tRNA synthetase mutants for efficient labeling of proteins with azidonorleucine in vivo," PNAS, vol. 106, No. 36, pp. 15285-15290 (2009).
Guo, J., et al., "Addition of an $\alpha$-Hydroxy Acid to the Genetic Code of Bacteria," Angew. Chem. Int. Ed., vol. 47, pp. 722-725 (2008).
Ellman, J. A., et al., "Site-Specific Incorporation of Novel Backbone Structures into Proteins," Science, vol. 255, pp. 197-200 (1992).
Lu, T., et al., "Probing ion permeation and gating in a K+ channel with backbone mutations in the selectivity filter," Nature Neuro., vol. 4, No. 3, pp. 239-246 (2001).

(Continued)

*Primary Examiner* — Kagnew H Gebreyesus
(74) *Attorney, Agent, or Firm* — Birch, Stewart, Kolasch & Birch, LLP (57) ABSTRACT A non-natural protein having at least one ester bond in its polypeptide main chain is synthesized by using an in vivo translation system in a ribosome. The following components (a) to (c) are expressed in a cell or an cell extraction solution in the presence of an $\alpha$-hydroxy acid: (a) an aminoacyl-tRNA synthetase which can activate the $\alpha$-hydroxy acid; (b) suppressor tRNA which can bind to the $\alpha$-hydroxy acid in the presence of the aminoacyl-tRNA synthetase; and (c) a gene encoding a desired protein having a nonsense mutation or a frame-shift mutation at a desired site.

7 Claims, 4 Drawing Sheets (56) References Cited

OTHER PUBLICATIONS

Li, Y., et al., "Ligation of Expressed Protein α-Hydrazides via Genetic Incorporation of an α-Hydroxy Acid," ACS Chem. Biol. (2012, in press).

European Search Report dated Dec. 3, 2010—EP 08851711.5.

Kobayashi, T., et al., "Recognition of Non-α-amino Substrates by Pyrrolysyl-tRNA Synthetase," J. Mol. Biol., vol. 385, pp. 1352-1360 (2009).

Owczarek, A., et al., "Enzymatic tRNA Acylation by Acid and α-Hydroxy Acid Analogues of Amino Acids," Biochem., vol. 47, pp. 301-307 (2008).

* cited by examiner

FIG. 1

Pyrrolysine (Pyl)

$N_\varepsilon$-Boc-lysine(Boc-Lys)

6-amino-N-Boc-2-hydroxyhexanoic acid
(Boc-Lys HA)

SEQUENCE LISTING

```
<160> NUMBER OF SEQ ID NOS: 9

<210> SEQ ID NO 1
<211> LENGTH: 1365
<212> TYPE: DNA
<213> ORGANISM: Methanosarcina mazeii
<220> FEATURE:
<221> NAME/KEY: CDS
<222> LOCATION: (1)..(1365)

<400> SEQUENCE: 1 atg gat aaa aaa cca cta aac act ctg ata tct gca acc ggg ctc tgg      48
Met Asp Lys Lys Pro Leu Asn Thr Leu Ile Ser Ala Thr Gly Leu Trp
1               5                   10                  15 atg tcc agg acc gga aca att cat aaa ata aaa cac cac gaa gtc tct      96
Met Ser Arg Thr Gly Thr Ile His Lys Ile Lys His His Glu Val Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 20  |     |     |     | 25  |     |     |     | 30  |     |     |     |     |      |
| cga | agc | aaa | atc | tat | att | gaa | atg | gca | tgc | gga | gac | cac | ctt | gtt | gta | 144  |
| Arg | Ser | Lys | Ile | Tyr | Ile | Glu | Met | Ala | Cys | Gly | Asp | His | Leu | Val | Val |      |
|     |     | 35  |     |     |     | 40  |     |     |     | 45  |     |     |     |     |     |      |
| aac | aac | tcc | agg | agc | agc | agg | act | gca | aga | gcg | ctc | agg | cac | cac | aaa | 192  |
| Asn | Asn | Ser | Arg | Ser | Ser | Arg | Thr | Ala | Arg | Ala | Leu | Arg | His | His | Lys |      |
|     |     | 50  |     |     |     | 55  |     |     |     | 60  |     |     |     |     |     |      |
| tac | agg | aag | acc | tgc | aaa | cgc | tgc | agg | gtt | tcg | gat | gag | gat | ctc | aat | 240  |
| Tyr | Arg | Lys | Thr | Cys | Lys | Arg | Cys | Arg | Val | Ser | Asp | Glu | Asp | Leu | Asn |      |
| 65  |     |     |     | 70  |     |     |     | 75  |     |     |     | 80  |     |     |     |      |
| aag | ttc | ctc | aca | aag | gca | aac | gaa | gac | cag | aca | agc | gta | aaa | gtc | aag | 288  |
| Lys | Phe | Leu | Thr | Lys | Ala | Asn | Glu | Asp | Gln | Thr | Ser | Val | Lys | Val | Lys |      |
|     |     |     | 85  |     |     |     | 90  |     |     |     | 95  |     |     |     |     |      |
| gtc | gtt | tct | gcc | cct | acc | aga | acg | aaa | aag | gca | atg | cca | aaa | tcc | gtt | 336  |
| Val | Val | Ser | Ala | Pro | Thr | Arg | Thr | Lys | Lys | Ala | Met | Pro | Lys | Ser | Val |      |
|     |     | 100 |     |     |     | 105 |     |     |     | 110 |     |     |     |     |     |      |
| gcg | aga | gcc | ccg | aaa | cct | ctt | gag | aat | aca | gaa | gcg | gca | cag | gct | caa | 384  |
| Ala | Arg | Ala | Pro | Lys | Pro | Leu | Glu | Asn | Thr | Glu | Ala | Ala | Gln | Ala | Gln |      |
|     |     | 115 |     |     |     | 120 |     |     |     | 125 |     |     |     |     |     |      |
| cct | tct | gga | tct | aaa | ttt | tca | cct | gcg | ata | ccg | gtt | tcc | acc | caa | gag | 432  |
| Pro | Ser | Gly | Ser | Lys | Phe | Ser | Pro | Ala | Ile | Pro | Val | Ser | Thr | Gln | Glu |      |
|     | 130 |     |     |     | 135 |     |     |     | 140 |     |     |     |     |     |     |      |
| tca | gtt | tct | gtc | ccg | gca | tct | gtt | tca | aca | tca | ata | tca | agc | att | tct | 480  |
| Ser | Val | Ser | Val | Pro | Ala | Ser | Val | Ser | Thr | Ser | Ile | Ser | Ser | Ile | Ser |      |
| 145 |     |     |     | 150 |     |     |     | 155 |     |     |     |     |     |     | 160 |      |
| aca | gga | gca | act | gca | tcc | gca | ctg | gta | aaa | ggg | aat | acg | aac | ccc | att | 528  |
| Thr | Gly | Ala | Thr | Ala | Ser | Ala | Leu | Val | Lys | Gly | Asn | Thr | Asn | Pro | Ile |      |
|     |     |     | 165 |     |     |     | 170 |     |     |     | 175 |     |     |     |     |      |
| aca | tcc | atg | tct | gcc | cct | gtt | cag | gca | agt | gcc | ccc | gca | ctt | acg | aag | 576  |
| Thr | Ser | Met | Ser | Ala | Pro | Val | Gln | Ala | Ser | Ala | Pro | Ala | Leu | Thr | Lys |      |
|     |     | 180 |     |     |     | 185 |     |     |     | 190 |     |     |     |     |     |      |
| agc | cag | act | gac | agg | ctt | gaa | gtc | ctg | tta | aac | cca | aaa | gat | gag | att | 624  |
| Ser | Gln | Thr | Asp | Arg | Leu | Glu | Val | Leu | Leu | Asn | Pro | Lys | Asp | Glu | Ile |      |
|     |     | 195 |     |     |     | 200 |     |     |     | 205 |     |     |     |     |     |      |
| tcc | ctg | aat | tcc | ggc | aag | cct | ttc | agg | gag | ctt | gag | tcc | gaa | ttg | ctc | 672  |
| Ser | Leu | Asn | Ser | Gly | Lys | Pro | Phe | Arg | Glu | Leu | Glu | Ser | Glu | Leu | Leu |      |
|     | 210 |     |     |     | 215 |     |     |     | 220 |     |     |     |     |     |     |      |
| tct | cgc | aga | aaa | aaa | gac | ctg | cag | cag | atc | tac | gcg | gaa | gaa | agg | gag | 720  |
| Ser | Arg | Arg | Lys | Lys | Asp | Leu | Gln | Gln | Ile | Tyr | Ala | Glu | Glu | Arg | Glu |      |
| 225 |     |     |     | 230 |     |     |     | 235 |     |     |     | 240 |     |     |     |      |
| aat | tat | ctg | ggg | aaa | ctc | gag | cgt | gaa | att | acc | agg | ttc | ttt | gtg | gac | 768  |
| Asn | Tyr | Leu | Gly | Lys | Leu | Glu | Arg | Glu | Ile | Thr | Arg | Phe | Phe | Val | Asp |      |
|     |     |     | 245 |     |     |     | 250 |     |     |     | 255 |     |     |     |     |      |
| agg | ggt | ttt | ctg | gaa | ata | aaa | tcc | ccg | atc | ctg | atc | cct | ctt | gag | tat | 816  |
| Arg | Gly | Phe | Leu | Glu | Ile | Lys | Ser | Pro | Ile | Leu | Ile | Pro | Leu | Glu | Tyr |      |
|     |     | 260 |     |     |     | 265 |     |     |     | 270 |     |     |     |     |     |      |
| atc | gaa | agg | atg | ggc | att | gat | aat | gat | acc | gaa | ctt | tca | aaa | cag | atc | 864  |
| Ile | Glu | Arg | Met | Gly | Ile | Asp | Asn | Asp | Thr | Glu | Leu | Ser | Lys | Gln | Ile |      |
|     | 275 |     |     |     | 280 |     |     |     | 285 |     |     |     |     |     |     |      |
| ttc | agg | gtt | gac | aag | aac | ttc | tgc | ctg | aga | ccc | atg | ctt | gct | cca | aac | 912  |
| Phe | Arg | Val | Asp | Lys | Asn | Phe | Cys | Leu | Arg | Pro | Met | Leu | Ala | Pro | Asn |      |
| 290 |     |     |     | 295 |     |     |     | 300 |     |     |     |     |     |     |     |      |
| ctt | tac | aac | tac | ctg | cgc | aag | ctt | gac | agg | gcc | ctg | cct | gat | cca | ata | 960  |
| Leu | Tyr | Asn | Tyr | Leu | Arg | Lys | Leu | Asp | Arg | Ala | Leu | Pro | Asp | Pro | Ile |      |
| 305 |     |     |     | 310 |     |     |     | 315 |     |     |     | 320 |     |     |     |      |
| aaa | att | ttt | gaa | ata | ggc | cca | tgc | tac | aga | aaa | gag | tcc | gac | ggc | aaa | 1008 |
| Lys | Ile | Phe | Glu | Ile | Gly | Pro | Cys | Tyr | Arg | Lys | Glu | Ser | Asp | Gly | Lys |      |
|     |     |     | 325 |     |     |     | 330 |     |     |     | 335 |     |     |     |     |      |
| gaa | cac | ctc | gaa | gag | ttt | acc | atg | ctg | aac | ttc | tgc | cag | atg | gga | tcg | 1056 |

-continued

```
                Glu His Leu Glu Glu Phe Thr Met Leu Asn Phe Cys Gln Met Gly Ser
                                    340                 345                 350 gga tgc aca cgg gaa aat ctt gaa agc ata att acg gac ttc ctg aac          1104
Gly Cys Thr Arg Glu Asn Leu Glu Ser Ile Ile Thr Asp Phe Leu Asn
            355                 360                 365 cac ctg gga att gat ttc aag atc gta ggc gat tcc tgc atg gtc tat          1152
His Leu Gly Ile Asp Phe Lys Ile Val Gly Asp Ser Cys Met Val Tyr
370                 375                 380 ggg gat acc ctt gat gta atg cac gga gac ctg gaa ctt tcc tct gca          1200
Gly Asp Thr Leu Asp Val Met His Gly Asp Leu Glu Leu Ser Ser Ala
385                 390                 395                 400 gta gtc gga ccc ata ccg ctt gac cgg gaa tgg ggt att gat aaa ccc          1248
Val Val Gly Pro Ile Pro Leu Asp Arg Glu Trp Gly Ile Asp Lys Pro
                405                 410                 415 tgg ata ggg gca ggt ttc ggg ctc gaa cgc ctt cta aag gtt aaa cac          1296
Trp Ile Gly Ala Gly Phe Gly Leu Glu Arg Leu Leu Lys Val Lys His
            420                 425                 430 gac ttt aaa aat atc aag aga gct gca agg tcc ggg tct tac tat aac          1344
Asp Phe Lys Asn Ile Lys Arg Ala Ala Arg Ser Gly Ser Tyr Tyr Asn
        435                 440                 445 ggg att tct acc aac ctg taa                                              1365
Gly Ile Ser Thr Asn Leu
    450
```

<210> SEQ ID NO 2
<211> LENGTH: 454
<212> TYPE: PRT
<213> ORGANISM: Methanosarcina mazeii

<400> SEQUENCE: 2

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
```

```
            210                 215                 220
Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
                260                 265                 270

Ile Glu Arg Met Gly Ile Asp Asn Asp Thr Glu Leu Ser Lys Gln Ile
            275                 280                 285

Phe Arg Val Asp Lys Asn Phe Cys Leu Arg Pro Met Leu Ala Pro Asn
        290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
                340                 345                 350

Gly Cys Thr Arg Glu Asn Leu Glu Ser Ile Ile Thr Asp Phe Leu Asn
            355                 360                 365

His Leu Gly Ile Asp Phe Lys Ile Val Gly Asp Ser Cys Met Val Tyr
370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Gly Ser Tyr Tyr Asn
            435                 440                 445

Gly Ile Ser Thr Asn Leu
    450

<210> SEQ ID NO 3
<211> LENGTH: 72
<212> TYPE: RNA
<213> ORGANISM: Methanosarcina mazeii

<400> SEQUENCE: 3
ggaaaccuga ucauguagau cgaauggacu cuaaauccgu ucagccgggu uagauucccg      60
ggguuuccgc ca                                                         72

<210> SEQ ID NO 4
<211> LENGTH: 12
<212> TYPE: DNA
<213> ORGANISM: Artificial Sequence
<220> FEATURE:
<223> OTHER INFORMATION: Eukaryotic type II promoter Box A consensus
      sequence
<220> FEATURE:
<221> NAME/KEY: misc_feature
<222> LOCATION: (5)..(5)
<223> OTHER INFORMATION: n = a,t,g or c
<220> FEATURE:
<221> NAME/KEY: misc_feature
<222> LOCATION: (6)..(6)
<223> OTHER INFORMATION: n = a,t,g or c
<220> FEATURE:
<221> NAME/KEY: misc_feature
<222> LOCATION: (10)..(10)
<223> OTHER INFORMATION: n = a,t,g or c
```

<400> SEQUENCE: 4
trgcnnagyn gg                                                                                      12

<210> SEQ ID NO 5
<211> LENGTH: 11
<212> TYPE: DNA
<213> ORGANISM: Artificial Sequence
<220> FEATURE:
<223> OTHER INFORMATION: Eukaryotic type II promoter Box B consensus
      sequence
<220> FEATURE:
<221> NAME/KEY: misc_feature
<222> LOCATION: (8)..(8)
<223> OTHER INFORMATION: n = a,t,g or c

<400> SEQUENCE: 5
ggttcgantc c                                                                                       11

<210> SEQ ID NO 6
<211> LENGTH: 504
<212> TYPE: PRT
<213> ORGANISM: Artificial Sequence
<220> FEATURE:
<223> OTHER INFORMATION: GST with T7 anf His-tag sequences

<400> SEQUENCE: 6

Met Ala Ser Met Thr Gly Gly Gln Gln Met Gly Arg Asp Pro Gly Ala
1               5                   10                  15

Asn Ser Gly Val Thr Lys Asn Ser Tyr Ser Pro Ile Leu Gly Tyr Trp
            20                  25                  30

Lys Ile Lys Gly Leu Val Gln Pro Thr Arg Leu Leu Leu Glu Tyr Leu
        35                  40                  45

Glu Glu Lys Tyr Glu Glu His Leu Tyr Glu Arg Asp Glu Gly Asp Lys
    50                  55                  60

Trp Arg Asn Lys Lys Phe Glu Leu Gly Leu Glu Phe Pro Asn Leu Pro
65                  70                  75                  80

Tyr Tyr Ile Asp Gly Asp Val Lys Leu Thr Gln Ser Met Ala Ile Ile
                85                  90                  95

Arg Tyr Ile Ala Asp Lys His Asn Met Leu Gly Gly Cys Pro Lys Glu
            100                 105                 110

Arg Ala Glu Ile Ser Met Leu Glu Gly Ala Val Leu Asp Ile Arg Tyr
        115                 120                 125

Gly Val Ser Arg Ile Ala Tyr Ser Lys Asp Phe Glu Thr Leu Lys Val
    130                 135                 140

Asp Phe Leu Ser Lys Leu Pro Glu Met Leu Lys Met Phe Glu Asp Arg
145                 150                 155                 160

Leu Cys His Lys Thr Tyr Leu Asn Gly Asp His Val Thr His Pro Asp
                165                 170                 175

Phe Met Leu Tyr Asp Ala Leu Asp Val Val Leu Tyr Met Asp Pro Met
            180                 185                 190

Cys Leu Asp Ala Phe Pro Lys Leu Val Cys Phe Lys Lys Arg Ile Glu
        195                 200                 205

Ala Ile Pro Gln Ile Asp Lys Tyr Leu Lys Ser Ser Lys Tyr Ile Ala
    210                 215                 220

Trp Pro Leu Gln Gly Trp Gln Ala Thr Phe Gly Gly Asp His Pro
225                 230                 235                 240

Pro Lys Ser Asp Leu Glu His His His His His Met Ala Ser Met
                245                 250                 255

```
Thr Gly Gly Gln Gln Met Gly Arg Asp Pro Gly Ala Asn Ser Gly Val
            260                 265                 270

Thr Lys Asn Ser Tyr Ser Pro Ile Leu Gly Tyr Trp Lys Ile Lys Gly
        275                 280                 285

Leu Val Gln Pro Thr Arg Leu Leu Leu Glu Tyr Leu Glu Lys Tyr
    290                 295                 300

Glu Glu His Leu Tyr Glu Arg Asp Glu Gly Asp Lys Trp Arg Asn Lys
305                 310                 315                 320

Lys Phe Glu Leu Gly Leu Glu Phe Pro Asn Leu Pro Tyr Tyr Ile Asp
                325                 330                 335

Gly Asp Val Lys Leu Thr Gln Ser Met Ala Ile Ile Arg Tyr Ile Ala
            340                 345                 350

Asp Lys His Asn Met Leu Gly Gly Cys Pro Lys Glu Arg Ala Glu Ile
        355                 360                 365

Ser Met Leu Glu Gly Ala Val Leu Asp Ile Arg Tyr Gly Val Ser Arg
    370                 375                 380

Ile Ala Tyr Ser Lys Asp Phe Glu Thr Leu Lys Val Asp Phe Leu Ser
385                 390                 395                 400

Lys Leu Pro Glu Met Leu Lys Met Phe Glu Asp Arg Leu Cys His Lys
                405                 410                 415

Thr Tyr Leu Asn Gly Asp His Val Thr His Pro Asp Phe Met Leu Tyr
            420                 425                 430

Asp Ala Leu Asp Val Val Leu Tyr Met Asp Pro Met Cys Leu Asp Ala
        435                 440                 445

Phe Pro Lys Leu Val Cys Phe Lys Lys Arg Ile Glu Ala Ile Pro Gln
    450                 455                 460

Ile Asp Lys Tyr Leu Lys Ser Ser Lys Tyr Ile Ala Trp Pro Leu Gln
465                 470                 475                 480

Gly Trp Gln Ala Thr Phe Gly Gly Asp His Pro Pro Lys Ser Asp
                485                 490                 495

Leu Glu His His His His His His
            500
```

<210> SEQ ID NO 7
<211> LENGTH: 678
<212> TYPE: DNA
<213> ORGANISM: Artificial Sequence
<220> FEATURE:
<223> OTHER INFORMATION: Grb2 suppression reporter gene
<220> FEATURE:
<221> NAME/KEY: CDS
<222> LOCATION: (1)..(678)
<223> OTHER INFORMATION: suppressor mutated Grb2 protein including FLAG
      tag
<220> FEATURE:
<221> NAME/KEY: misc_feature
<222> LOCATION: (331)..(333)
<223> OTHER INFORMATION: Amber codon
<220> FEATURE:
<221> NAME/KEY: misc_feature
<222> LOCATION: (652)..(675)
<223> OTHER INFORMATION: FLAG tag

<400> SEQUENCE: 7

```
atg gaa gcc atc gcc aaa tat gac ttc aaa gct act gca gac gac gag      48
Met Glu Ala Ile Ala Lys Tyr Asp Phe Lys Ala Thr Ala Asp Asp Glu
1               5                   10                  15 ctg agc ttc aaa agg ggg gac atc ctc aag gtt ttg aac gaa gaa tgt      96
Leu Ser Phe Lys Arg Gly Asp Ile Leu Lys Val Leu Asn Glu Glu Cys
            20                  25                  30
```

```
gat cag aac tgg tac aag gca gag ctt aat gga aaa gac ggc ttc att    144
Asp Gln Asn Trp Tyr Lys Ala Glu Leu Asn Gly Lys Asp Gly Phe Ile
         35                  40                  45 ccc aag aac tac ata gaa atg aaa cca cat ccg tgg ttt ttt ggc aaa    192
Pro Lys Asn Tyr Ile Glu Met Lys Pro His Pro Trp Phe Phe Gly Lys
 50                  55                  60 atc ccc aga gcc aag gca gaa gaa atg ctt agc aaa cag cgg cac gat    240
Ile Pro Arg Ala Lys Ala Glu Glu Met Leu Ser Lys Gln Arg His Asp
 65                  70                  75                  80 ggg gcc ttt ctt atc cga gag agt gag agc gct cct ggg gac ttc tcc    288
Gly Ala Phe Leu Ile Arg Glu Ser Glu Ser Ala Pro Gly Asp Phe Ser
                 85                  90                  95 ctc tct gtc aag ttt gga aac gat gtg cag cac ttc aag gtg tag cga    336
Leu Ser Val Lys Phe Gly Asn Asp Val Gln His Phe Lys Val     Arg
            100                 105                 110 gat gga gcc ggg aag tac ttc ctc tgg gtg gtg aag ttc aat tct ttg    384
Asp Gly Ala Gly Lys Tyr Phe Leu Trp Val Val Lys Phe Asn Ser Leu
                115                 120                 125 aat gag ctg gtg gat tat cac aga tct aca tct gtc tcc aga aac cag    432
Asn Glu Leu Val Asp Tyr His Arg Ser Thr Ser Val Ser Arg Asn Gln
        130                 135                 140 cag ata ttc ctg cgg gac ata gaa cag gtg cca cag cag ccg aca tac    480
Gln Ile Phe Leu Arg Asp Ile Glu Gln Val Pro Gln Gln Pro Thr Tyr
145                 150                 155 gtc cag gcc ctc ttt gac ttt gat ccc cag gag gat gga gag ctg ggc    528
Val Gln Ala Leu Phe Asp Phe Asp Pro Gln Glu Asp Gly Glu Leu Gly
160                 165                 170                 175 ttc cgc cgg gga gat ttt atc cat gtc atg gat aac tca gac ccc aac    576
Phe Arg Arg Gly Asp Phe Ile His Val Met Asp Asn Ser Asp Pro Asn
                180                 185                 190 tgg tgg aaa gga gct tgc cac ggg cag acc ggc atg ttt ccc cgc aat    624
Trp Trp Lys Gly Ala Cys His Gly Gln Thr Gly Met Phe Pro Arg Asn
            195                 200                 205 tat gtc acc ccc gtg aac cgg aac gtc gac tac aag gac gac gat gac    672
Tyr Val Thr Pro Val Asn Arg Asn Val Asp Tyr Lys Asp Asp Asp Asp
        210                 215                 220 aag tga                                                            678
Lys
```

<210> SEQ ID NO 8
<211> LENGTH: 110
<212> TYPE: PRT
<213> ORGANISM: Artificial Sequence
<220> FEATURE:
<223> OTHER INFORMATION: Grb2 suppression reporter gene

<400> SEQUENCE: 8

```
Met Glu Ala Ile Ala Lys Tyr Asp Phe Lys Ala Thr Ala Asp Asp Glu
 1               5                  10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Lys Pro His Pro Trp Phe Phe Gly Lys
 50                  55                  60

Ile Pro Arg Ala Lys Ala Glu Glu Met Leu Ser Lys Gln Arg His Asp
 65                  70                  75                  80

Gly Ala Phe Leu Ile Arg Glu Ser Glu Ser Ala Pro Gly Asp Phe Ser
                85                  90                  95
```

```
Leu Ser Val Lys Phe Gly Asn Asp Val Gln His Phe Lys Val
            100                 105                 110

<210> SEQ ID NO 9
<211> LENGTH: 114
<212> TYPE: PRT
<213> ORGANISM: Artificial Sequence
<220> FEATURE:
<223> OTHER INFORMATION: Grb2 suppression reporter gene

<400> SEQUENCE: 9

Arg Asp Gly Ala Gly Lys Tyr Phe Leu Trp Val Val Lys Phe Asn Ser
1               5                   10                  15

Leu Asn Glu Leu Val Asp Tyr His Arg Ser Thr Ser Val Ser Arg Asn
                20                  25                  30

Gln Gln Ile Phe Leu Arg Asp Ile Glu Gln Val Pro Gln Gln Pro Thr
            35                  40                  45

Tyr Val Gln Ala Leu Phe Asp Phe Asp Pro Gln Glu Asp Gly Glu Leu
    50                  55                  60

Gly Phe Arg Arg Gly Asp Phe Ile His Val Met Asp Asn Ser Asp Pro
65                  70                  75                  80

Asn Trp Trp Lys Gly Ala Cys His Gly Gln Thr Gly Met Phe Pro Arg
                85                  90                  95

Asn Tyr Val Thr Pro Val Asn Arg Asn Val Asp Tyr Lys Asp Asp Asp
                100                 105                 110

Asp Lys
```

PROCESS FOR PRODUCTION OF NON-NATURAL PROTEIN HAVING ESTER BOND THEREIN

This application is the national stage of International Application PCT/JP2008/071221, filed Nov. 21, 2008, which claims priority under 35 USC 119(a)-(d) of Japanese Application No. 2007-302452 filed Nov. 22, 2007.

REFERENCE TO RELATED APPLICATION

This application is based upon the priority of Japanese patent application No. 2007-302452, filed on Nov. 22, 2007, the disclosure of which is incorporated herein in its entirety by reference thereto.

TECHNICAL FIELD

The present invention relates to a process for production of non-natural protein having ester bond therein. In more detail, the present invention relates to a method of a site-specific introduction of an α-hydroxy acid into a protein using an aminoacyl-tRNA synthetase and a ribosomal translation system.

BACKGROUND

Based on a progress of a technological development regarding a recent protein translation system, a synthesis of various peptides and proteins incorporating non-natural amino acids is capable. For developing a new bioactive substance and creating a technological high-performance nano-device, these non-natural compositions become an important technical base. However, a shortage of non-natural basic unit applicable to the translation system in a cell has been an obstacle for synthesizing a wide variety of non-natural peptides and non-natural proteins.

For adding new function to a protein, it is pointed out that not only a side chain structure of a polypeptide but also a structure of the polypeptide backbone play an important role. For example, it is known that once one amide bond is replaced by an ester bond at a tranmembrane domain of membrane protein, a hydrogen bond derived from a peptide bond of the backbone is destroyed, which affects great influence on permeability of the protein into the membrane and agonist activity (see, for example, non-patent document 1). There are several methods to replace the amide bond of the polypeptide backbone into the ester bond site-specifically in order to synthesize such non-natural proteins.

A first method is to introduce the α-hydroxy acid into a polypeptide based on the genetic code, in vitro or micro-injectionable cell (see, for example, non-patent documents 2 and 3). The α-hydroxy acid is introduced into in vitro translational system by binding it to tRNA corresponding to non-sense codon (an amber codon, a 4 characters codon, and the like) according to not enzymatic but organic chemical reaction. Thereby, the α-hydroxy acid is introduced into the polypeptide with the translational reaction in the ribosome at non-sense codon specifically. However, in this method, once a tRNA bound with the α-hydroxy acid is used in the reaction, the tRNA itself needs not to be reused. Accordingly, tRNAs (20-40 μM) bound with the α-hydroxy acid more than the number of the molecules of the polypeptide to synthesize must be synthesized with organic chemical reaction, and introduced into a test tube. Its organic chemical manipulation is so complicated and takes a cost. In addition, a polypeptide yield including the α-hydroxy acid synthesized in such system is very low.

Secondly, there is a method of in vitro introduction of the α-hydroxy acid into a polypeptide based on a genetic code using a ribozyme (see, for example, non-patent document 4). The α-hydroxy acid is introduced into in vitro translational system by binding it to tRNA corresponding to non-sense codon (an amber codon, a 4 characters codon, and the like) according to enzymatic reaction. Thereby, the α-hydroxy acid is introduced into the polypeptide with the translational reaction in the ribosome at non-sense codon specifically. However, in this method too, once the tRNA bound with the α-hydroxy acid is used in the reaction, the tRNA needs not to be reused. Accordingly, there is the same problem as described above, concerning the manipulation complicatedness and the production yield.

Thirdly, an introduction technique of non-natural amino acids within a living cell using the aminoacyl-tRNA synthetase (aaRS) and the tRNA is raised. In this method, an extraneous aaRS originally recognizing non-natural amino acid or artificially modified to recognize non-natural amino acid and a gene of a suppressor tRNA which is recognized by the above extraneous aaRS and recognizes a non-sense codon, are introduced into a living cell like *E. coli* and expressed in the cell. Thereby, the non-natural amino acid is enzymatically bound to the suppressor tRNA within the cell, and the non-natural amino acid is site-specifically introduced into a peptide (a protein) by the translational reaction in the ribosome. As a combination of the aaRS and the tRNA, an achaebacterium tyrosyl-tRNA synthetase (TyrRS) and an amber suppressor tRNA$^{Tyr}$ mutant, a lysyl-tRNA synthetase and a tRNA corresponding to 4 characters codon, a pyrrolysyl-tRNA synthetase (PylRS) and a tRNA$^{Pyl}$ (see, for example, patent document 1) are used in *E. coli*, and a bacterium TyrRS and an amber suppressor tRNA$^{Tyr}$ mutant (see, for example, non-patent document 5), a leucyl-tRNA synthetase and an amber suppressor tRNA$^{Leu}$ mutant, the PylRS and the tRNA$^{Pyl}$ are used in eukaryote. However, in either enzyme, because of a specificity against an α-amino acid inherited in the aaRS, it has not succeeded yet in introducing the α-hydroxy acid so far, even if it has succeeded in introducing the α-amino acid having different side chain with artificial modification. In addition, it has been considered that such modification is actually difficult.

Fourthly, it is reported as an example that the α-hydroxy acid is introduced into a protein with a special in vitro translational system, in which the α-hydroxy acid corresponding to methionine is bound to the corresponding tRNA enzymatically using E-coli methionyl-tRNA synthetase (see, for example, non-patent document 6). This method is efficient because the α-hydroxy acid is bound to tRNA enzymatically many times in the reaction solution of in vitro translational system via a cycle that tRNA is used in ribosome. However, there are problems that the translational system itself should have a special composition of the aminoacyl-tRNA synthetase and the tRNA, and the α-hydroxy acid is introduced into all methionine codons. Moreover, this can not be used in a living cell.

[Patent Document 1] Japanese Patent Kokai Publication No. JP2007-037445A
[Non-Patent Document 1] England P M, Zhang Y, Dougherty D A, Lester H A. "Backbone mutations in transmembrane domains of a ligand-gated ion channel: implications for the mechanism of gating", Cell 96, 89-98 (1999)
[Non-Patent Document 2] Koh J T, Cornish V W, Schultz P G. "An experimental approach to evaluating the role of backbone interactions in proteins using unnatural amino acid mutagenesis", Biochemistry 36, 11314-11322 (1997)

[Non-Patent Document 3] Chapman E, Thorson J S, Schultz P G. "Mutational analysis of backbone hydrogen bonds in staphylococcal nuclease", J. Am. Chem. Soc. 119, 7151-7152 (1997)

[Non-Patent Document 4] Murakami H, Ohta A, Ashigai H, Suga H. "A highly flexible tRNA acylation method for non-natural polypeptide synthesis", Nat. Methods 3, 357-359 (2006)

[Non-Patent Document 5] Wang L, Brock A, Herberich B, Schultz P G. "Expanding the genetic code of Escherichia coli", Science 292, 498-500 (2001)

[Non-Patent Document 6] Hartman M C, Josephson K, Lin C W, Szostak J W. "An expanded set of amino Acid analogs for the ribosomal translation of unnatural peptides", PLoS ONE 2, e972 (2007)

The entire disclosures of the above patent document 1 and non-patent documents 1-6 are incorporated herein by reference thereto. The following analysis is given by the present invention.

As described in the above, the basic unit which can be linked has been only amino acid or derivative thereof in the in vivo translational system from the point of view in a substrate specificity of the aaRS. However, if the peptide bond of the backbone composing protein is replaced with the ester bond efficiently using in vivo translational system in the ribosome, it will be useful for synthesizing a variety of non-natural proteins.

In a process of researching the structure and functions of the aaRS, inventors of the present invention have found that the pyrrolysyl-tRNA synthetase (PylRS) which is an aminoacyl-tRNA synthetase inherited in partial achaebacterum and bacterium recognizes the α-hydroxy acid within E. coli and mammal cells, and the α-hydroxy acid could be specifically introduced into a stop codon of mRNA. And, using such a reaction system, they succeeded in enzymatic synthesizing a non-natural protein including an ester bond in a desired position in a polypeptide backbone within a living cell for the first time.

That is to say, a method of producing an unnatural protein of the present invention is characterized in that: expressing (a) an aminoacyl-tRNA synthetase capable of activating an α-hydroxy acid, (b) a suppressor tRNA capable of binding to the α-hydroxy acid in the presence of said aminoacyl-tRNA synthetase, and (c) a gene encoding a desired protein that has a nonsense mutation or frameshift mutation at a desired site, in a cell or cell extract solution in the presence of said α-hydroxy acid.

It is preferred that the aminoacyl-tRNA synthetase is a pyrrolysyl-tRNA synthetase (PylRS) derived from archaebacterium, or a mutant thereof. Further, it is preferred that the mutant pyrrolysyl-tRNA synthetase comprises an amino acid substitution of at least one amino acid residue selected from alanine at position 302, tyrosine at position 306, leucine at position 309, asparagine at 346, cysteine at position 348, tyrosine at position 384 and tryptophan at 417, in the amino acid sequence of a wild type pyrrolysyl-tRNA synthetase represented by SEQ ID NO:2.

In a preferred mode of the present invention, the amino acid substitution in the mutant pyrrolysyl-tRNA synthetase comprises at least one amino acid substitutions of: from alanine to phenylalanine at position 302; from tyrosine to alanine at position 306; from leucine to alanine at position 309; from asparagine to serine at position 346; from cysteine to valine or isoleucine at position 348; and from tyrosine to phenylalanine at position 384. In one mode, the mutant enzyme defined in the present invention is PylRS (Y384F), PylRS (Y306A), PylRS (L309A, C348V), and PylRS (A302F, Y306A, N346S, C348I, Y384F).

In another preferred mode, the α-hydroxy acid is an N-substituted 6-amino-2-hydroxyhexanoic acid, or an optionally substituted 3-phenyllacetic acid. It is further preferred that the substituent at amino group of the N-substituted 6-amino-2-hydroxyhexanoic acid is t-butoxycarbonyl group, or an optionally substituted phenyl group, benzyl group or benzyloxycarbonyl group. In one mode, the α-hydroxy acid defined in the present invention is 6-amino-N-Boc-2-hydroxyhexanoic acid, 6-amino-benzyloxycarbonyl-2-hydroxyhexanoic acid, 3-phenyllacetic acid.

When the α-hydroxy acid is introduced into the polypeptide, it is bound as an ester bond which is different from the usual amide bond. Compared to the amide bond, the ester bond can be easily cleaved by acid or alkali. Thus, it is applicable to prepare (and the like) a cleavable tag depending on pH at a desired position in a protein. Moreover, it is possible to modify a conformation of the protein into a new conformation that can not be achieved in amide bond. Because the ester bond can be introduced based on genetic information, an ester bond-introduced polypeptide having a certain (or specific) activity can be selected by a genetic screening method. Among such polypeptides, it is considered that there is a polypeptide having a new beneficial function that a conventional polymer consisting of only amino acids does not have.

PREFERRED MODES

Aminoacyl-tRNA Synthetase (aaRS)

The aaRS usable for the present invention can activate the α-hydroxy acid, and can recognize the suppressor tRNA and bind the α-hydroxy acid to the suppressor tRNA. The aaRS is not restricted to a naturally-existing aaRS or a mutant enzyme, as far as the aaRS has such characteristics; however, it is preferably a pyrrolysyl-tRNA synthetase (PylRS) derived from archaebacterium, especially methanogenic archaebacterium. Inventors of the present invention found that a wild-type PylRS or a PylRS in which a residue of a pocket region recognizing the side chain portion of amino acid is modified recognizes not only an α-amino acid that can be recognized respectively but also the α-hydroxy acid having the same side chain as the α-amino acid.

As the wild-type PylRS, for example, but not restricted to these, it can be derived from Methanosarcina mazei, Methanosarcina barkeri, Methanosarcina acetivorans and the like which are methanogeneic archaebacterium. Many bacterium genomic nucleotide sequences including these archaebacterium and amino acid sequences thereof are well known, and it is possible to obtain other homological PylRS by homological searching of nucleotide sequences and amino acid sequences based on public database like GenBank, for example. As a typical example, a PylRS derived from *Methanosarcina mazei* is registered as accession number AAM31141, a PylRS derived from *Methanosarcina barkeri* is registered as accession number AAL40867, and a PylRS derived from *Methanosarcina acetivorans* is registered as accession number AAM03608. Especially, the PylRS derived from *Methanosarcina mazei* is preferred, its genetic nucleotide sequence is shown as SEQ ID NO:1, and amino acid sequence of its protein is shown as SEQ ID NO:2. Sequences of these *Methanosarcina* genus's PylRS homologue are well-preserved, for example, a homology of amino acid sequences is approximately 70% or above. These wild-type PylRSs recognize pyrrolysine side chain as a substrate. However, it is considered that a mutant PylRS recognizing a desired side chain structure can be synthesized by introducing a mutation into its substrate binding site.

[Synthesis of a Mutant aaRS]

The mutant aaRS defined in the present invention can be synthesized by modifying the substrate binding site so as to recognize a desired α-hydroxy acid. Although various aaRS's configurations are already disclosed; however, among them, it is preferred to use the PylRS derived from archaebacterium. Inventors of the present invention have already reported about a crystallization of catalytic domein and an x-ray crystallography of the PylRS derived from *Methanosarcina mazei* (Yanagisawa, T. et al., Acta Cryst. (2006)F62, 1031-1033). In addition, regarding various mutant enzymes synthesized based on the configuration of the PylRS, a Patent application as JP 2007-243574 was already filed on Sep. 20, 2007 according to the Applicant of the present application. These disclosures are incorporated herein by reference thereto.

For an amino acid substrate recognition of the PylRS, an existence of a carbonyl binding to E amino group of lysine and a hydrophobic functional group attached to a tip (or terminal side) of the carbonyl binding is important. If the hydrophobic functional group has a certain level of size and bulky volume such as a pyrrol ring, the wild-type PylRS can activate its lysine derivative. However, there is a limitation of the lysine derivative's size which the wild-type PylRS can activate, and for example, the wild-type PylRS can not efficiently recognize a lysine derivative having a large functional group such as $N^\epsilon$-benzyloxycarbonyl-lysine (Z-Lys), for instance.

Therefore, a desired mutant enzyme can be obtained by introducing a mutation into a substrate binding site of the PylRS in order to recognize the α-hydroxy acid having various side chain structures. The PylRS derived from *Methanosarcina mazei* has 454 amino acid residues and it is mainly composed of two domains. The C terminal domain of about 250 amino acid residues has 7 anti-parallel β-sheets specified to aaRS in class-II, and a pyrrolysine molecule is bound onto its surface. 4-methyl-pyrroline ring characterized with bulky volume of pyrrolysine is accommodated in a tunnel formed by mainly a hydrophobic residue, including, of Ala-302, Leu-305, Tyr-306, Leu-309, Cys-348, Val-401, Leu-407, Ile-413 and Trp-417 in the amino acid sequence shown in SEQ ID NO:2. Accordingly, a wide variety of mutant PylRS that the substrate specificity are different can be synthesized by replacing any residue or several residues of these amino acid residues with other amino acid(s).

Inventors of the present invention already found that an activity against Boc-Lys is increased for the mutant PylRS (Y384F) having replacement from tyrosine to phenylalanine at position 384 in the wild-type PylRS, and an activity against Z-Lys derivative is increased for the mutant PylRS (Y306A) having replacement from tyrosine to alanine at position 306 in the wild-type PylRS. In addition, an activity against Z-Lys derivative is increased for a double mutant PylRS (L309A, C348V) having replacements from leucine to alanine at position 309 and from cysteine to valine at position 348 in the wild-type PylRS. Moreover, they found that a quintuple mutant PylRS (A302F, Y306A, N346S, C348I, Y384F) having replacements from alanine to phenylalanine at position 302, from tyrosine to alanine at position 306, from asparagine to serine at position 346, from cysteine to isoleucine at position 348, and from tyrosine to phenylalanine at position 384 recognizes the phenylalanine as a substrate. Accordingly, it is considered to introduce the corresponding α-hydroxy acid by using these mutants PylRS.

As a method to synthesize such a mutant, various methods well-known to a person skilled in the art can be used. For example, using a primer in which a nucleotide sequence coding a targeted amino acid position is replaced with a nucleotide sequence coding an amino acid that should be modified, a DNA that is replaced with a nucleotide sequence coding an amino acid to be modified is amplified with PCR to obtain a full-length DNA coding the mutant PylRS, and then the resultant DNA can be expressed using a host cell such as *E. coli* and the like. Alternatively, the method can be performed with the well-known site-specific mutation method such as Kunkel method or Gapped duplex method and the like, and a mutation kit (for example, Mutan-K and Mutan-G (supplied by TaKaRa) and the like) using these well-known method can be used.

[α-Hydroxy Acid]

Figure 1:
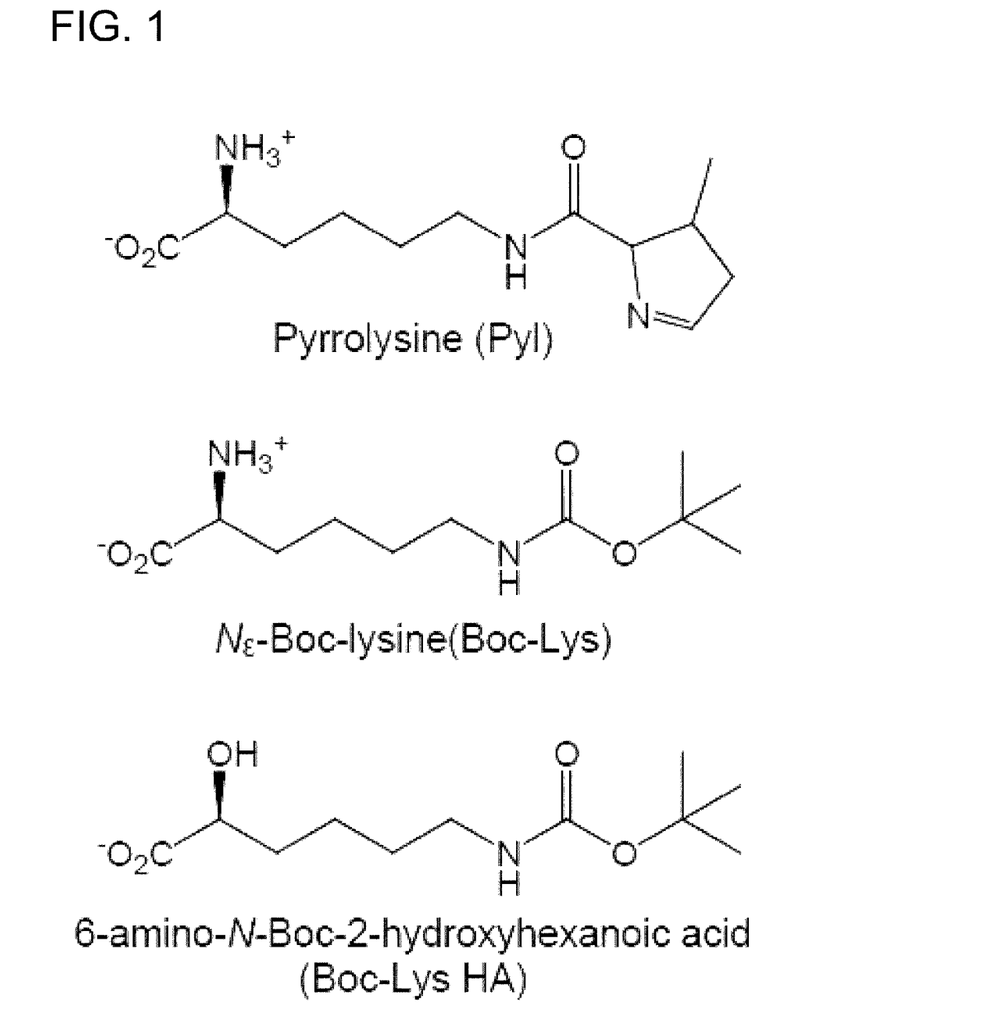
FIG. 1 shows a structure of a substrate amino acid or the α-hydroxy acid recognized by the wild-type PylRS.

As the α-hydroxy acid used in the present invention, it may be these which can be recognized by the above described aaRS, without restriction. Preferably, however, it is a α-hydroxy acid recognized by the wild-type PylRS and the mutant PylRS. As shown in FIG. 1, the wild-type PylRS can recognize $N^\epsilon$-tert-butoxycarbonyl-lysine (Boc-Lys) which is well-resembled with the side chain structure of pyrrolysine (Pyl) and its corresponding α-hydroxy acid as 6-amino-N-Boc-2-hydroxyhexanoic acid (Boc-Lys-HA). Moreover, it is acknowledged that the wild-type PylRS esterifies tRNA$^{Pyl}$ with $N^\epsilon$-modified lysine derivative like allyloxycarbonyl-lysine (Aloc-Lys), $N^\epsilon$-acetyl-L-lysine (Ac-Lys), $N^\epsilon$-nicotinyl-L-lysine (Nic-Lys), $N^\epsilon$-benzyloxycarbonyl-L-lysine (Z-Lys) and $N^\epsilon$-(N-methyl-anthranyroyl)-L-lysine (Nma-Lys), and the α-hydroxy acid corresponding to these derivatives can be used.

The α-hydroxy acid used in the preferred embodiment of the present invention is an N-substituted 6-amino-2-hydroxyhexanoic acid, or substituted 3-phenyllacetic acid. The substituted group of amino acid in the N-substituted 6-amino-2-hydroxyhexanoic acid is t-butoxycarbonyl group, or phenyl group, benzyl group, or benzyloxycarbonyl (Z) group, which may optionally have a substituted group. As a substituted group of the Z group, for example, crosslinker (azido, diaziline) or a reactive functional group (alkyne) and the like are included at ortho position. Concretely, $N^\epsilon$-ortho-iodo-benzyloxycarbonyl-2-hydroxyhexanoic acid, $N^\epsilon$-ortho-ethinyl-benzyloxycarbonyl-2-hydroxyhexanoic acid, $N^\epsilon$-ortho-azido-benzyloxycarbonyl-2-hydroxyhexanoic acid, $N^\epsilon$-ortho-diaziryl-benzyloxycarbonyl-2-hydroxyhexanoic acid and the like are listed.

In addition, a substituted group at 3 position in the substituted 3-phenyllacetic acid is a phenyl group which may optionally have a substituted group, and concretely, 3-(3-iodophenyl) lactic acid, 3-(3-bromophenyl) lactic acid, 3-(4- acetylphenyl) lactic acid, 3-(4-benzoylphenyl) lactic acid, 3-(4-azidophenyl) lactic acid, 3-(3-methyl-4-hydroxyphenyl) lactic acid and the like are listed.

[Suppressor tRNA]

A tRNA used combined with the above aaRS is assigned to a nonsense codon which is a codon not assigned to usual 20 kinds amino acids, and also is recognized by only the above described aaRS. In addition, it has a condition not to be recognized by conventional aminoacyl-tRNA synthetase in a host (orthogonal tRNA), and also must be expressed within eubacterium or mammal cell. As a such tRNA, a suppressor tRNA derived from achaebacterium is listed.

Here, as the nonsense codon, UAG (amber), UAA (ochre), UGA (opal) are listed; however, it is preferable to use UAG (amber) or UGA (opal) codons. In addition, instead of using the nonsense codon, a codon composed of at least 4 nucleotides (preferably, 4 or 5 nucleotides) (hereinafter, it is called "frame-shift codon") can be also used.

For example, such a tRNA obtains a gene corresponding to tRNA$^{Pyl}$ from the above achaebacterium genome, then the obtained gene itself, or a desired mutation is introduced, is expressed in vitro or in vivo, and thereby a preparation can be performed. As one example, the wild-type tRNA derived from Methanosarcina mazei has a nucleotide sequence as follows.

(SEQ ID NO: 3)
tRNA$^{Pyl}$: 5'-GGAAACCUGAUCAUGUAGAUCGAAUGGAUUCUAAAUC
CGUUCAGCCGGGUUAGAUUCCCGGGGUUUCCGCCA-3'

[Production of Non-Natural Protein]

The aminoacyl-tRNA synthetase which can activate the α-hydroxy acid can be used for in vitro or in vivo producing a protein incorporating the α-hydroxy acid by combining the suppressor tRNA of achaebacterium or eukaryote. That is, the following (a), (b) and (c) are expressed within cell or cell extract (solution) under the existence of the α-hydroxy acid: (a) an aminoacyl-tRNA synthetaze which can activate the α-hydroxy acid, (b) a suppressor tRNA which can combine with the α-hydroxy acid under the existence of the aminoacyl-tRNA synthetase, (c) a gene coding a desired protein mutated with nonsense mutation or a frame-shift mutation at a desired position. Here, as a synthetic system of the aaRS or the suppressor tRNA related to the present invention, any expressing system can be used, without particular restriction. For example, a cell-free protein synthesizing system and a protein synthesizing system in eubacterium cell, or a eukaryote cell, preferably an animal cell, especially preferably a mammalian cell are listed.

The cell-free protein synthesizing system is a system that takes out the protein factor which is necessary for translation of the protein as cell extract (solution), and synthesizes an aimed protein by re-constituting this reaction in a test tube. The cell-free system can be constituted by using extract derived from various biological species, for example, extracts of bacterium like E. coli and thermophilic bacteria, an eukaryotic cell in high synthetic activity of protein like wheat germ agglutinin, rabbit reticulocyte, mouse L-cell, Ehrlich ascites tumor cell, HeLa cell, CHO cell and budding yeast, and a prokaryotic cell can be used (Clemens, M. J., Transcription and Translation—A Practical Approach, (1984), pp. 231-270, Henes, B. D. et al. eds., IRL Press, Oxford (reference 1)). Note, the content of reference 1 is incorporated herein by reference thereto.

As an extract from E. coli, a S30 extract prepared by methods described in Zubay et al (Zubay et al., Ann. Rev. genet. Vol. 7, pp. 267-287 (1973) (reference 2)) and Pratt et al (Pratt, J. M. et al., Transcription and Translation—A Practical Approach, (1984), pp. 179-209, Henes, B. D. et al. eds., IRL Press, Oxford (reference 3)) can be used. The E. coli S30 extract includes all enzymes and factors of E. coli necessary for transcription and translation. A complemental mixture can be added, too. A concrete method for preparation of E. coli S30 cell extract solution is as follows: First, E. coli cells are cultured and harvested by centrifugation and the like. The harvested bacterial cells are washed, and then resuspended in a buffer solution and destructed using French press, glass beads, Waring blender and the like. Insoluble substances of the destructed E. coli cells are removed by centrifugation, and the remaining is mixed with a pre-incubation mixture to be incubated. Endogenous DNA and RNA are degraded by this manipulation. In addition, however, it may be done to degrade endogenous nucleic acids by supplementation of a calcium salt, a nuclease of Micrococcus and the like. Subsequently, endogenous amino acid, nucleic acid, nucleoside etc. are removed by dialysis and the resulting solution is aliquoted to preserve in liquid nitrogen or at −80° C. In addition, the contents of the references 2 and 3 are incorporated herein by reference thereto.

When a synthetic reaction of the protein incorporating the α-hydroxy acid is performed, DNA or RNA coding a desired protein mutated with a non-sense mutation or a frame-sift mutation at a desired position in transcriptional/translational template; amino acid including the α-hydroxy acid; the mutant PylRS of the present invention; the suppressor tRNA which can bind with the α-hydroxy acid under the existence of the mutant PylRS; an energy source; various ions; a buffer solution; an ATP regenerating system; a nucleolytic enzyme inhibitor; tRNA; a reductant; polyethylene glycol; cAMP; folic acid and the like; an antibacterial agent; substrates of RNA synthesis and RNA polymerase and the like in the case where DNA is used as a template; can be included. These are prepared by appropriately selecting, depending on an aimed protein or a pattern of protein synthesizing system to be used. For example, in the case of the S30 extract of E. coli, a part of or all of the following listed are added; the listed are Tris-acetic acid, DTT, NTPs (ATP, CTP, GTP and UTP), phosphoenolpyruvate, pyruvate kinase, amino acids (in addition to natural 20 amino acids, phosphoserine is added), polyethylene glycol (PEG), folic acid, cAMP, tRNA, ammonium acetate, calcium acetate, potassium glutamate, and magnesium acetate at optimum density and the like.

In order to express the aaRS defined in the present invention within a mammalian cell, it should be performed that the aaRS gene is amplified by PCR method, and the amplified product is incorporated into a commercially available, expression vector like pcDNA3.1 (Invitrogen) at NheI-BamHI site, and then the composed plasmid is introduced into the mammalian cell. As an introducing method of a vector into a cell, for example, an electroporation, a calcium phosphate method, a lipofection and the like are listed.

On the other hand, as an expression method of the suppressor tRNA, it can be expressed within eubacterium of E. coli and the like or eukaryotic cell of mammalian cell and the like according to well-known methods for a person skilled in the art, without particular restriction. For example, for the expression within E. coli, a promoter sequence is bound to 5' terminal of DNA coding the suppressor tRNA and a terminator sequence is bound to 3' terminal of the above DNA, respectively. A type II promoter transcribing tRNA within eukaryotic cell is an internal promoter formed of two domains within tRNA coding sequence, and its consensus sequence is known as box A, box B. The consensus sequence of the box A is TRGCNNAGYNGG from 8 to 19 positions (SEQ ID NO:4), and the consensus sequence of the box B is GGTTC-GANTCC from 52 to 62 positions (SEQ ID NO:5). Accordingly, for example, in the case where there are box A and box B in the coding sequences like a suppressor tyrosine tRNA of *Bacillus stearothermophilus*, an expression is possible within the animal cell even if any modification is not added at all. However, in the case of the suppressor tRNA not having the internal promoter, an expression is possible within the eukaryotic cell using an external promoter, too. For example, the expression would be possible efficiently within the animal cell by binding tRNA nucleotide sequence of eukaryote or a promoter sequences of U1 or U6snRNA gene to 5' terminal of the suppressor tRNA gene. In addition, as a different embodiment, the suppressor tRNA may be expressed within an animal cell at the same time with T7 RNA polymerase by ligating T7 promoter derived from T7 phage.

The present invention is further described with reference to the following examples, which are not intended to restrict the scope of the present invention.

EXAMPLES

Example 1

Synthesis of the Non-Natural Protein Incorporating the α-Hydroxy Acid Using *E. Coli* Cell (1) Synthesis of α-Hydroxy Acid Boc-Lys-HA H-Lys (Boc)-OH (Bachem) as a raw material, it is organically synthesized based on a method of a reference (Organic Letters 6, 497-500 (2004)).

(2) Plasmid (2.1) PylRS/tRNA$^{Pyl}$ Expression System

The full-length PylRS gene was expressed under controlling of *E. coli* trpS promoter in plasmid pTK2-1. This plasmid pTK2-1 is a derivative of a plasmid pACYC184, and in which plasmid, one copy of tRNA$^{Pyl}$ gene is expressed under the controlling of kanamycin resistant gene and *E. coli* 1 pp promoter.

(2.2) Glutathione-5-transferase (GST) Expression System Incorporating an Ester Bond The glutathione-5-transferase (GST) gene in which a cysteine codon at 109 position from N terminal was mutated to amber codon (TAG) was cloned between NdeI-BamHI sites in pET21b (ampicillin resistance), and an expression vector such that the following protein added with T7 tag at its N terminal and histidine tag at its C terminal is synthesized was organized. Its amino acid sequence is as follows.

(SEQ ID NO: 6)
<u>MASMTGGQQMG</u>RDPGANSGVTKNSYSPILGYWKIKGLVQPTRLLLEYLE

EKYEEHLYERDEGDKWRNKKFELGLEFPNLPYYIDGDVKLTQSMAIIRY

IADKHNMLGG<u>C</u>PKERAEISMLEGAVLDIRYGVSRIAYSKDFETLKVDFL

SKLPEMLKMFEDRLCHKTYLNGDHVTHPDFMLYDALDVVLYMDPMCLDA

FPKLVCFKKRIEAIPQIDKYLKSSKYIAWPLQGWQATFGGGDHPPKSD<u>L

EHHHHHH</u>

The first underline (MASMTGGQQMG) including T7 tag, the last underline including histidine tag, and these regions are derived from pET21b. A codon corresponding to Cys109 shown in the middle underline is replaced with a sequence (TGA) corresponding to the amber codon.

(3) Expression and purification of the protein including the ester bond (3.1) The above two plasmids were introduced into BL21 (DE3) with general transformation method.

(3.2) The resultant was cultured through overnight at LB culture medium including ampicillin (100 μg/ml) and kanamycin (50 μg/mg). Its culturing was all incubated at 37° C., but the incubation temperature can be altered arbitrary to high or low depending on a protein to be expressed.

(3.3) From the obtained culture solution, bacterial cells were separated by the centrifugal separation. The separated bacterial cell was inoculated in a GMML culture medium including BocLys-HA (1 mM), ampicillin (100 μg/ml) and kanamycin (50 μg/mg) (1×M9 (Sigma-Aldrich M-6030), $MgSO_4$ (1 mM), $CaCl_2$ (0.1 mM), NaCl (8.5 mM), $Fe_2SO_4$ (5 μM), 1% glycerol, leucine (0.3 mM)).

(3.4) When turbidity is changed from 0.3 to 0.4 at wavelength 600 nm, an IPTG was added with a final concentration at 1 mM.

(3.5) It was cultured for 6 hours, and then bacteria cells were collected by centrifugation.

(3.6) The protein purification was performed using glutathione sepharose 4 fastflow (GE Healthcare) according to attached protocol.

(4) Verification that the Ester Bond has been Introduced.

(4.1) Regarding the obtained protein, a sample added with water (−OH) and a sample added with ammonia water in final concentration of 14% (+OH) were prepared, they are reacted for two hours at ambient temperature, respectively.

Figure 2:
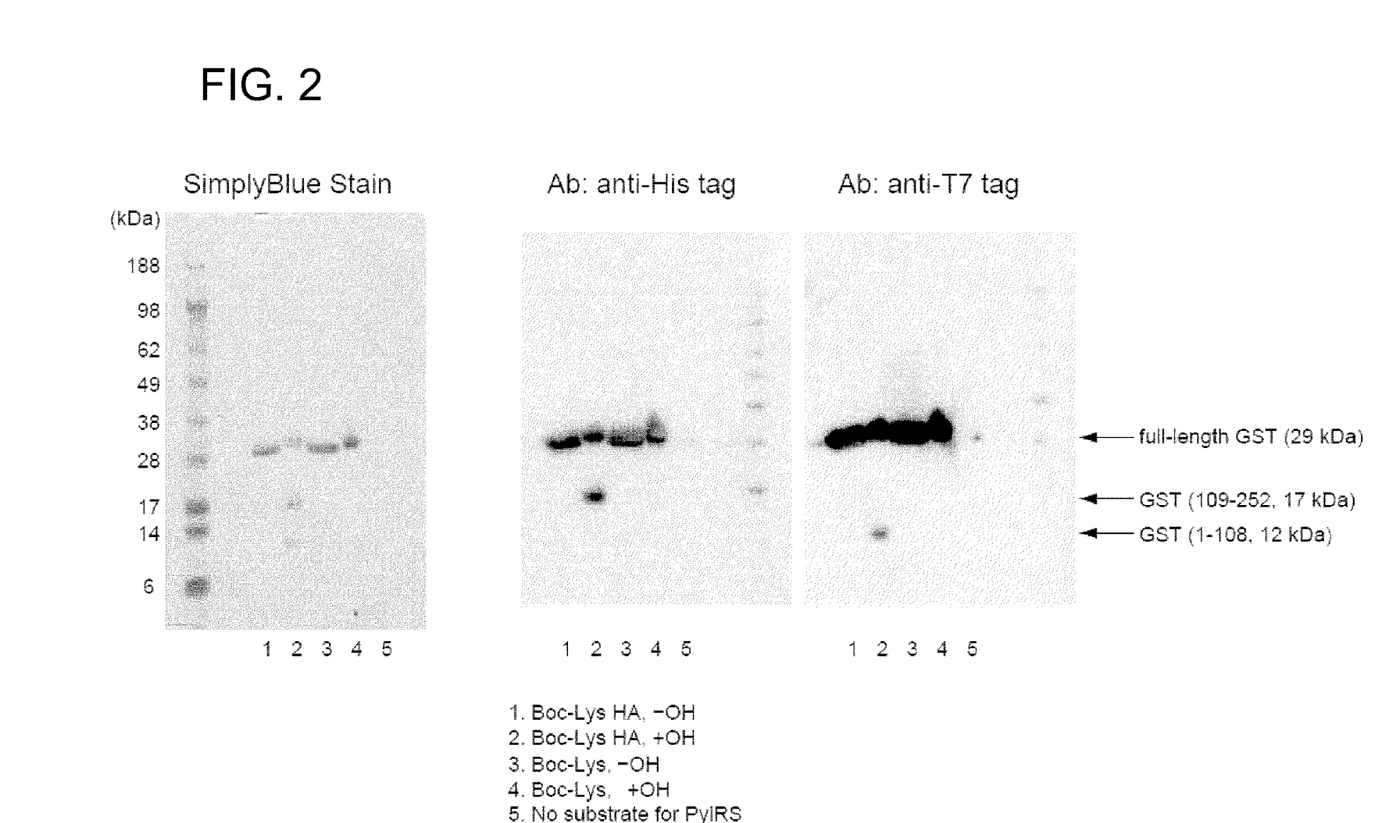
FIG. 2 shows a result that an alkali hydrolysis of a protein synthesized in Example 1 was analyzed by SDS-PAGE.

(4.2) For each sample, separation was performed with 12% SDS-polyacrylamide electrophoresis, and staining with SimplyIBlue Safe Stain (Invitrogen) was performed. As shown in FIG. 2, because a full-length GST was expressed only when BocLys-HA was added to the culture medium, and it was cleaved with specific cleavage at one position by ammonia water and two polypeptide were shown, thereby it is indicated that the ester bond is included in one position. For GMML culture medium, a protein yield was approximately 1 mg/L culture.

(4.3) From the gel which migrated as the same as (4.2), a polypeptide including T7 tag (N-terminal) and a polypeptide including histidine tag (C-terminal) were detected with antibodies specific to each polypeptide by Western blotting. As shown in FIG. 2, it was indicated that each expected band included respective tag. In the lane 5, the GST was expressed without adding non-natural substrate to the culture medium and the purified matter was migrated. No band is shown because suppression of amber codon does not occur. On the other hand, when Boc-Lys-HA and Boc-Lys were added, the full-length GST has been produced (lanes 1, 3). In the case where an alkali decomposition is performed, Boc-Lys-HA was introduced, and a cleavage occurs at a specific site only when the ester bond is included within the protein (lane 2). For Boc-Lys, a cleavage does not occur because of only having usual amide bond therein (lane 4). In the lane 2, the full-length GST is left because the migration was performed under a state that hydrolysis had not progressed completely.

Figure 3:
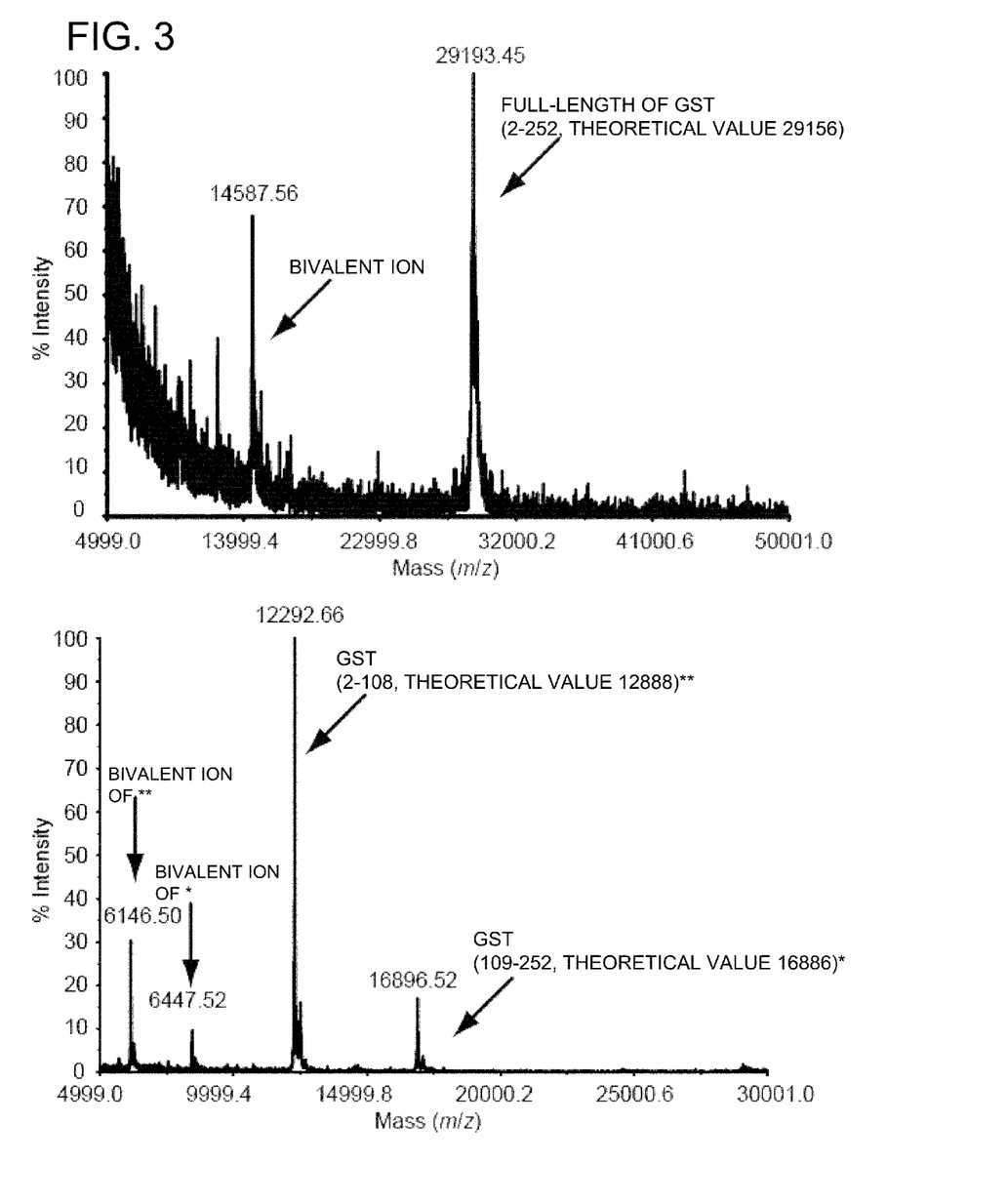
FIG. 3 shows a result of mass spectrum with MALDI-TOF of pre-alkali hydrolysis (upper) and post-alkali hydrolysis (below) of a GST including Boc-Lys-HA at 109 position.

(4.4) For the sample obtained in (4.1), cleavage reaction had completely progressed overnight, and its resultant was analyzed with a MALDI-TOF mass spectrometer. As shown in FIG. 3, main peak is one peak corresponding to respective band, and a probability that different amino acid was introduced at 109 position was excluded. In addition, each mass (result of mass spectrometry) shows that BocLys-HA has been introduced at 109 position and the only ester bond thereof was decomposed by alkali hydrolysis. In the case

Example 2

Introduction of Boc-Lys-HA into Protein for HEK293c-18 Strain (1) Cell which was Used
HEK293c-18 Strain (ATCC No. CRL-10852)
(2) Plasmid A leucine codon at 111 position in human grb2 was converted to an amber codon (grb2 (Am111)) by using Quick Change site-directed mutagenesis kit (Stratagene). Then, a gene (SEQ ID NO:7) which was constructed such that FLAG tag (DYKDDDDK) is added to C-terminal was incorporated into BamHI-XhoI site in pOriP vector, and this resultant was defined as a plasmid for detecting suppression. The Grb2 is a protein that is related to cell canceration, interacting with epidermal growth factor receptor within a cell.

A construction of PylRS expression plasmid was performed such that the wild-type PylRS gene DNA sequence (SEQ ID NO:1) derived from Methanosarcina mazei was amplified by using PCR method. This amplified product was incorporated into NheI-BamHI site in pOriP vector, to construct a plasmid.

For an expression vector of tRNA$^{Pyl}$ gene, the wild-type pyrrolysine tRNA gene derived from Methanosarcina mazei and terminator were linked to a downstream of human U6 promoter, and 9 copies of this linkage product aligned in one direction was incorporated into NruI-PvuII site in pOriP vector. Note, the pOriP is ones that a sequence between PvuII-PvuII of pcDNA4/TO (Invitrogen) is cut out and deleted, and MunI digestive fragment of pCEP4 (Invitrogen) is inserted at MunI site; thereby the pOriP raises transfection efficiency in a cell like HEK293c-18 strain expressing EBNA-1 protein.

(3) Transfection Method

Three kinds of plasmid produced in the above were dissolved in 50 µl of Opti-MEM. 2 µl of Lipofectamine 2000 was mixed with another 5 µl of Opti-MEM, and incubated for 5 minutes at ambient temperature. These solutions were mixed, and incubated for 20 minutes at ambient temperature, then after incubation, they were added in HEK 293 cell that was cultured 90-95% confluent, and cultured in a carbon dioxide incubator for 4 hours at 37° C. 4 hours later, the culture medium was exchanged to DMEM/F-12 including 10 mM of Boc-Lys-HA, and further it was cultured for 40 hours at 37° C.

(4) Assay Method

According to the above transfection, all genes of Grb2 (111Amb), PylRS, and tRNA$^{Pyl}$ were introduced into HEK293c-18 strain, and nothing was added to one well and Boc-Lys-HA was added to the other well. Cells were collected and an immuno-precipitation was performed with anti-FLAG antibody, and purified proteins were mixed with ammonia solution or water and separated with 15% SDS-PAGE and a Western-blotting was performed, then they were immuno-stained with anti-FLAG antibody. Also, a condition of the ammonia treatment was that 10% SDS solution (5 µl) and ammonia solution (7.5 µl) were added into the purified protein (1 µl) and they were reacted for 2 hours at ambient temperature. After that, ammonia was removed with centrifugal vacuum. In the case where the ammonia treatment was not performed, 5 µl of water, instead of ammonia, was added into the purified protein and left it for 2 hours at ambient temperature.

(5) Result

Figure 4:
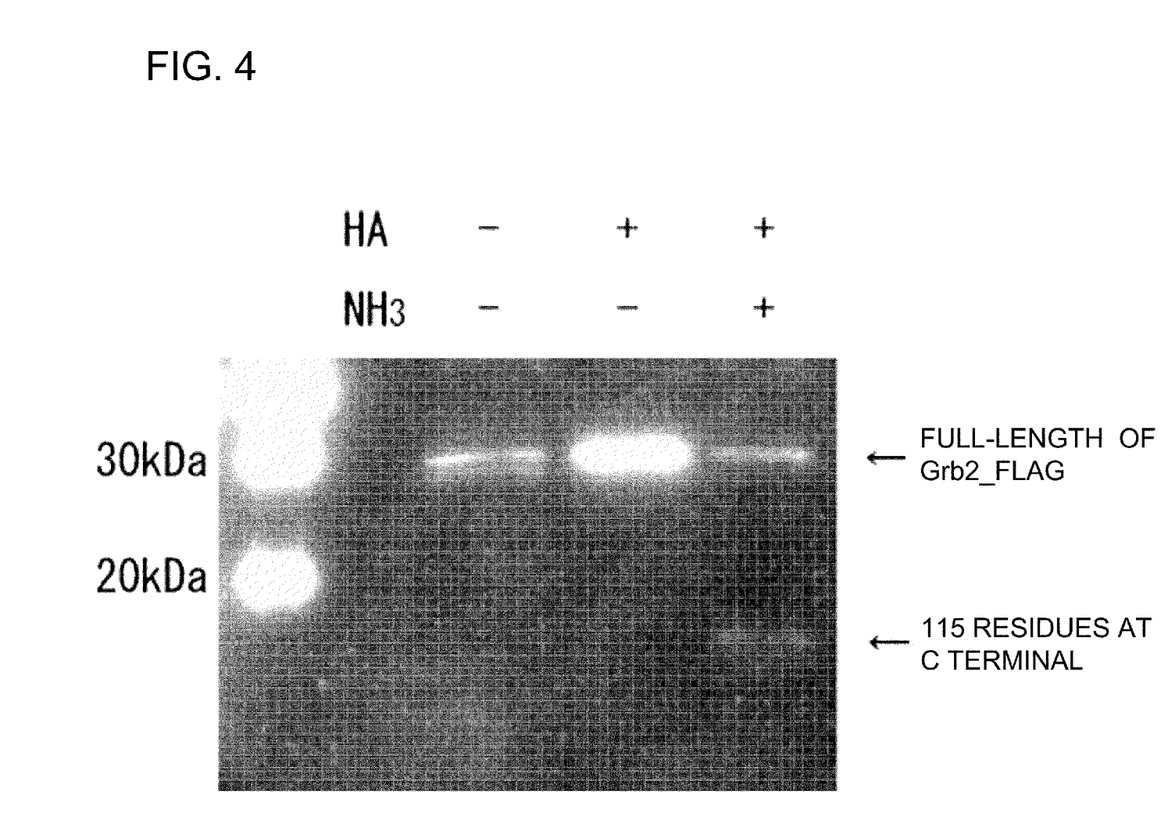
FIG. 4 shows a result that an alkali hydrolysis of a protein synthesized in Example 2 was analyzed by SDS-PAGE. Wherein, HA+/− shows presence or absence of a hydroxyl acid addition, and NH3+/− shows presence or absence of an ammonia treatment.

An experimental result in the above is shown in FIG. 4. According to FIG. 4, the hydroxy acid was introduced into the amber codon of Grb2 (111Amb) and the full-length 225 residues of Grb2_FLAG was expressed, and in the case of the ammonia treatment, the Grb2 was cut into a half and 115 residues at C terminal were detected (FLAG tag at C terminal was stained). Therefore, it was verified that the hydroxy acid has been introduced into the protein.

In addition, although the full-length of Grb2_FLAG was detected for the synthesized sample without adding the hydroxyl acid in FIG. 4, it is considered that an intrinsic suppression activity was detected because lots of purified proteins were applied in this example. Here, it is to be noted that the disclosures of the above mentioned Patent Documents etc. are all incorporated herein in their entireties by reference thereto. It should be noted that changes and modifications of the modes or Examples may be done within the entire disclosure (inclusive of the claims) of the present invention and on the basis of the basic technical concept thereof. Also, it should be noted that a variety of combinations or selections of various elements as disclosed may be made within the scope of the claims of the present invention. That is, it should be noted that the present invention also includes various changes and modifications which can be made by a person skilled in the art on the basis of all the disclosure (inclusive of the claims) and technical concept.

---

What is claimed:

1. A method of producing a cell or a cell extract having activity of incorporating an alpha-hydroxy acid into a polypeptide to provide a polypeptide having an ester bond in the main chain, comprising expressing
  - (a1) a pyrrolysyl-tRNA synthetase derived from an archaebacterium that is capable of activating an α-hydroxy acid that is N-substituted 6-amino-2-hydroxyhexanoic acid; or
  - (a2) a pyrrolysyl-tRNA synthetase having the amino acid sequence of SEQ ID NO: 2 and having at least one amino acid substitution of:
  from tyrosine to alanine at position 306,
  from leucine to alanine at position 309,
  from cysteine to valine at position 348, and
  from tyrosine to phenylalanine at position 384,
  and that is capable of activating an α-hydroxy acid that is N-substituted 6-amino-2-hydroxyhexanoic acid; or
  - (a3) pyrrolysyl-tRNA synthetase having the amino acid sequence of SEQ ID NO: 2 and having the five amino acid substitutions from alanine to phenylalanine at position 302, tyrosine to alanine at position 306, from asparagine to serine at position 346, from cysteine to isoleucine at position 348, and from tyrosine to phenylalanine at position 384, and that is capable of activating an α-hydroxy acid that is an optionally substituted 3-phenyllactic acid;
  - (b) a suppressor tRNA capable of binding to the α-hydroxy acid in the presence of said pyrrolysyl-tRNA, synthetase; and
  - (c) a gene encoding a desired protein that has a nonsense mutation or frameshift mutation at a desired site;
  in a cell or cell extract solution in the presence of said α-hydroxy acid.

2. The method of claim 1, wherein a substituent at the amino group of said N-substituted 6-amino-2-hydroxyhexanoic acid is t-butoxycarbonyl group, or an optionally substituted phenyl group, benzyl group or benzyloxycarbonyl group.

3. The method of claim 1, comprising expressing said (a1), (a2) or (a3), (b) and (c) in *Escherichia coli* cells.

4. The method of claim 1, comprising expressing said (a1), (a2) or (a3), (b) and (c) in mammalian cells.

5. A method for making an unnatural polypeptide that has at least one ester bond in a polypeptide main chain comprising culturing a cell expressing:
  - (a1) a pyrrolysyl-tRNA synthetase derived from an archaebacterium that is capable of activating an α-hydroxy acid that is N-substituted 6-amino-2-hydroxyhexanoic acid; or
  - (a2) a pyrrolysyl-tRNA synthetase having the amino acid sequence of SEQ ID NO: 2 and having at least one amino acid substitution of:
  from tyrosine to alanine at position 306,
  from leucine to alanine at position 309,
  from cysteine to valine at position 348, and
  from tyrosine to phenylalanine at position 384,
  and that is capable of activating an α-hydroxy acid that is N-substituted 6-amino-2-hydroxyhexanoic acid; or
  - (a3) pyrrolysyl-tRNA synthetase having the amino acid sequence of SEQ ID NO: 2 and having the five amino acid substitutions from alanine to phenylalanine at position 302, tyrosine to alanine at position 306, from asparagine to serine at position 346, from cysteine to isoleucine at position 348, and from tyrosine to phenylalanine at position 384, and that is capable of activating an α-hydroxy acid that is an optionally substituted 3-phenyllactic acid;

(b) a suppressor tRNA capable of binding to the α-hydroxy acid in the presence of said aminoacyl-tRNA synthetase; and (c) a gene encoding a desired protein that has a nonsense mutation or frameshift mutation at a desired site;

in the presence of said α-hydroxy acid.

6. The method of claim 1, in which the pyrrolysyl-tRNA synthetase is a mutant enzyme selected from the group consisting of substitution Y384F, substitution Y306A, the double substitution Y306A/Y384F and the double substitution L309A/C348V, in the amino acid sequence of SEQ ID NO:2.

7. The method of claim 5, in which the pyrrolysyl-tRNA synthetase is a mutant enzyme selected from the group consisting of substitution Y384F, substitution Y306A, the double substitution Y306A/Y384F and the double substitution L309A/C348V, in the amino acid sequence of SEQ ID NO:2.

* * * * *